United States Patent [19]

Cantor et al.

[11] Patent Number: 4,839,293
[45] Date of Patent: Jun. 13, 1989

[54] DNA ENCODING STREPTAVIDIN, STREPTAVIDIN PRODUCED THEREFROM, FUSED POLYPEPTIDES WHICH INCLUDE AMINO ACID SEQUENCES PRESENT IN STREPTAVIDIN AND USES THEREOF

[75] Inventors: Charles R. Cantor; Richard Axel; Carlos Argarana, all of New York, N.Y.

[73] Assignee: The Trustees of Columbia University in the City of New York, New York, N.Y.

[21] Appl. No.: 833,324

[22] Filed: Feb. 24, 1986

[51] Int. Cl.⁴ .................. C12N 15/00; C12P 21/00; C12P 21/02; C07H 15/12
[52] U.S. Cl. ...................... 435/320; 435/68; 435/70; 435/172.3; 435/240.2; 435/317.1; 435/252.33; 435/235; 536/27; 935/11; 935/29; 935/32; 935/47; 935/48
[58] Field of Search .............. 536/27; 435/70, 172.3, 435/240, 253, 317, 849

[56] References Cited

U.S. PATENT DOCUMENTS 4,356,270 10/1982 Itakura ........................... 435/317
4,438,032  3/1984 Golde et al. .................... 260/112 R
4,478,914 10/1984 Giese ............................ 428/407
4,617,261 10/1986 Sheldon et al. .................. 435/6

FOREIGN PATENT DOCUMENTS 0128332 12/1984 European Pat. Off. .

Primary Examiner—Elizabeth C. Weimar
Assistant Examiner—Thomas D. Mays
Attorney, Agent, or Firm—John P. White; John J. Santalone

[57] ABSTRACT

DNA which encodes the polypeptide streptavidin has been isolated as a fragment 2 kb in length derived from a restriction endonuclease digestion of the chromosomal DNA of *Streptomyces avidinii*. The nucleic acid sequence of the gene and the amino acid sequence of the polypeptide have been determined. A fused gene has been prepared which comprises the streptavidin gene fused to a gene encoding the human LDL receptor. Expression of the gene fusion results in a fused streptavidin-human LDL receptor polypeptide. Methods are provided for using the fused gene to produce labeled, chemically modified proteins in vivo and to isolate a protein knowing only the nucleotide sequence of the gene encoding the protein.

25 Claims, 8 Drawing Sheets

Figure 1

Amino acid sequence determined from the gel-purified protein

```
 1                                    10
Asp Pro Ser Lys Asp Ser Lys Ala Gln Val Ser Ala Ala Glu Ala
                20                                        30
Gly Ile Thr Gly Thr Trp Tyr Asn Gln Leu Gly Ser Thr Phe Ile
                                    40
Val Thr Ala Gly Ala Asp Gly Ala Leu Thr
```

Oligonucleotide probes used

```
                                     7   8   9   10
Amino acid sequence                 Lys Ala Gln Val
Possible codons                  5' AAA GCN CAA GUN 3'
                                     G       G Probe Stv11                         TTT CGN GTT CA
                                     C       C 21  22  23  24  25
Amino acid sequence                 Trp Tyr Asn Gln Leu
Possible codons                  5' UGG UAU AAU CAA CUN 3'
                                         C   C   G  UUU
                                                     C
Probe Stv14                         ACC ATA TTA GTT GA
                                         G   G   C  A
```

Figure 3

```
1        5'   CCCTCCGTCCCCGCCGGGCAACAACTAGGGAGTATTTTTCGTGTCTCAC
                  -20                                           -10
         Met Arg Lys Ile Val Val Ala Ala Ile Ala Val Ser Leu Thr Thr
     50  ATG CGC AAG ATC GTC GTT GCA GCC ATC GCC GTT TCC CTG ACC ACG
             MstI                                     1
         Val Ser Ile Thr Ala Ser Ala Ser Ala Asp Pro Ser Lys Asp Ser
     95  GTC TCG ATT ACG GCC AGC GCT TCG GCA GAC CCC TCC AAG GAC TCG
                             10                              20
         Lys Ala Gln Val Ser Ala Ala Glu Ala Gly Ile Thr Gly Thr Trp
    140  AGG GCC CAG GTC TCG GCC GCC GAG GCC GGC ATC ACC GGC ACC TGG
                                         30
         Tyr Asn Gln Leu Gly Ser Thr Phe Ile Val Thr Ala Gly Ala Asp
    185  TAC AAC CAG CTC GGC TCG ACC TTC ATC GTG ACC GCG GGC GCC GAC
                             40                              50
         Gly Ala Leu Thr Gly Thr Tyr Glu Ser Ala Val Gly Asn Ala Glu
    230  GGC GCC CTG ACC GGA ACC TAC GAG TCG GCC GTC GGC AAC GCC GAG
                                         60
         Ser Arg Tyr Val Leu Thr Gly Arg Tyr Asp Ser Ala Pro Ala Thr
    275  AGC CGC TAC GTC CTG ACC GGT CGT TAC GAC AGC GCC CCG GCC ACC
                             70                              80
         Asp Gly Ser Gly Thr Ala Leu Gly Trp Thr Val Ala Trp Lys Asn
    320  GAC GGC AGC GGC ACC GCC CTC GGT TGG ACG GTG GCC TGG AAG AAT
                                         90
         Asn Tyr Arg Asn Ala His Ser Ala Thr Thr Trp Ser Gly Gln Tyr
    365  AAC TAC CGC AAC GCC CAC TCC GCG ACC ACG TGG AGC GGC CAG TAC
                            100                             110
         Val Gly Gly Ala Glu Ala Arg Ile Asn Thr Gln Trp Leu Leu Thr
    410  GTC GGC GGC GCC GAG GCG AGG ATC AAC ACC CAG TGG CTG CTG ACC
                                        120
         Ser Gly Thr Thr Glu Ala Asn Ala Trp Lys Ser Thr Leu Val Gly
    455  TCC GGC ACC ACC GAG GCC AAC GCC TGG AAG TCC ACG CTG GTC GGC
                            130                             140
         His Asp Thr Phe Thr Lys Val Lys Pro Ser Ala Ala Ser Ile Asp
    500  CAC GAC ACC TTC ACC AAG GTG AAG CCG TCC GCC GCC TCC ATC GAC
                                        150
         Ala Ala Lys Lys Ala Gly Val Asn Asn Gly Asn Pro Leu Asp Ala
    545  GCG GCG AAG AAG GCC GGC GTC AAC AAC GGC AAC CCG CTC GAC GCC
                                    HincII
         Val Gln Gln Stop
    590  GTT CAG CAG TAG TCGCGTCCCGGCACCGGCGGGTGCCGGGACCTCGGCC  3'
```

Figure 4

```
                                                         10
                                      Streptav.  D P S K D S K A Q V S
                     10                           20
Avidin     A R K C S L T G K W T N D L G S N M T I G A V N S R G
                          20                      30
Streptav.  A A E A G I T G T W N Q L G S T F I V T A G A D G A 30                    40                        50
Avidin     E F T G T Y T T A V T A T S N E I K E S P L H G T E N
              40                    50                   60
Streptav.  L T G T Y E S A V G N A E S R Y V L T G R Y D S A P A 60                    70                    80
Avidin     T I N K R T Q P T E G E T V N W K F S E S T T V F T G
                          70                    80                    90
Streptav.  T D G S G T A L G W T V A W K N Y R N A H S A T T W 90                     100
Avidin     Q C F I D R N G K E V L K T M W L L R S V N D I G D
                          100                     110
Streptav.  S G Q Y V G G A E A R I N T Q W L L T S G T T E A N A 110                 120
Avidin     D W K A T R V G I N I F T R L R T Q K E
              120                 130                  140
Streptav.  W K S T L V G H D T F T K V K P S A A S I D A A K K A 150
Streptav.  G V N N G N P L D A V Q Q
```

Figure 5

```
                                                      Streptav. DPSKDSKAQVS
                                                                 1
                 1            20                 40
Avidin       ARKCSLTGKWTNDLGSNMTIGAVNSRGEFTGTYTTAVTATSNEIKESPLHG
              B  α    T     B                    B      T B
Streptav.    AAEAGITGTWYNQLGSTFIVTAGADGALTGTYESAVGNAESRYVLTGRYDS
                  20               40                        60

60                 80                   100
Avidin       TENTINKRTQPTFGFTVNWKFSESTTVFTGQCFIDRNGKEVLKTMWLLRSS
                 T   B          T     B       T         B
Streptav.    APATDGSGTALGWTVAWKNNYRNAHSATTWSGQYVGGAEARINTQWLLTSG
                             80                    100

120
Avidin       VNDIGDDWKATRVGINIFTRLRTQKE
              T α    T
Streptav.    TTEANAWKSTLVGHDTFTKVKPSAASIDAAKKAGVNNGNPLDAVQQ
                 120                  140
```

DNA ENCODING STREPTAVIDIN, STREPTAVIDIN PRODUCED THEREFROM, FUSED POLYPEPTIDES WHICH INCLUDE AMINO ACID SEQUENCES PRESENT IN STREPTAVIDIN AND USES THEREOF

Certain embodiments of the invention described herein were made in the course of work under Grant No. GM 14825-19, from the National Institutes of Health, U.S. Department of Health and Human Services. The U.S. Government has certain rights in this invention.

BACKGROUND OF THE INVENTION

Throughout this application various publications are referenced by arabic numerals within parentheses. Full citations for these refernces may be found at the end of the specification immediately preceding the claims. The disclosures of these publications in their entireties are hereby incorporated by reference into this application in order to more fully describe the state of the art as known to those skilled therein as of the date of the invention described and claimed herein.

Streptavidin, a protein produced by Streptomyces avidinii, forms a very strong and specific non-covalent complex with the water-soluble vitamin biotin. Streptavidin was discovered in 1963 (1) as part of an antibiotic system in culture filtrates of several species of Streptomyces. Later Chaiet and Wolf (2) established its chemical nature and determined its amino acid composition. Streptavidin is a nearly neutral 60,000 dalton protein. It consists of 4 identical subunits each having an approximate molecular weight of 15,000 daltons. Streptavidin binds 4 molecules of biotin per molecule of protein, and it is free of carbohydrate. Avidin, a basic glycoprotein usually isolated from chicken egg-whites, shares with streptavidin some common characteristics such as molecular weight, subunit composition and capacity to bind biotin and forming a complex with biotin of very high affinity ($K_D = 10^{-15}$) (3-4). Streptavidin and avidin have different amino acid compositions, but both have an unusually high content of threonine and tryptophan. Although streptavidin and avidin (derived from egg-white) bind biotin with equally high affinity, streptavidin has the advantage of avoiding much of the undesirable, nonspecific binding associated with avidin at physiological pH. The reasons for this are: (1) the isoelectric point of streptavidin is close to neutral, that of avidin is 10 (thus avidin is positively charged at pH 7.0); and (2) streptavidIn contains no carbohydrate, while avidin contains approximately 7% carbohydrate.

At present, commercial preparations of streptavidin made by growing S. avidinii have several disadvantages: they are high in cost and are frequently contaminated with biotin, and, as a result do not have all four valences free for binding biotin. Furthermore, production of streptavidin from S. avidinii yields only limited quantities of streptavidin.

The present invention overcomes the disadvantages of present commercial preparations of streptavidin by providing an inexpensive source of streptavidin, which is essentially free of biotin contamination, and has all four valences free for biotin binding. The present invention contemplates vectors which can produce streptavidin in large quantities. Furthermore, improved streptavidins may be produced by site-directed mutagenesis.

There have been attempts in the past to devise methods for labeling and detecting small amounts of interesting proteins within living cells. Past methods have included fusing to genes encoding the interesting proteins a prokaryotic gene, e.g. the gene for beta-galactosidase. Expression of the resulting fused gene results in a fused polypeptide, e.g. one containing the amino acid sequence from beta-galactosidase which can be used for stabilization and isolation of the protein of interest. However, such methods could not be used to produce labeled proteins in vivo.

The present invention provides a method of generating labeled proteins in vivo, without the need for in vivo covalent chemical modification. The present method utilizes a marker protein which may be non-covalently attached to a tag which remains with the protein. This method may be used to produce labeled proteins in vivo or to isolate target proteins knowing only the structure of the gene which encodes them.

Biotin may be conjugated to a variety of biological molecules using the strong, specific biotin binding capacity of avidin or streptavidin. The fused gene of the present invention thus permits the detection, localization or purification of proteins, carbohydrates and nucleic acids.

SUMMARY OF THE INVENTION

DNA which encodes the polypeptide streptavidin has been isolated as a fragment 2 kb in length derived from a restriction endonuclease digestion of the chromosomal DNA of *Streptomyces avidinii*. This DNA has the nucleic acid sequence set forth in FIG. 3. The 2 kb fragment contains the entire region encoding the streptavidin polypeptide, a region encoding a signal peptide and the flanking region DNA which occurs naturally at the 3' and 5' ends of the coding region. The DNA fragment has been introduced into a cloning vehicle which has been inserted into the genomic DNA of a bacterial host cell.

This invention also provides a fused gene which comprises a first DNA fragment encoding a target protein of interest fused to a DNA fragment encoding streptavidin, said streptavidin having a multiplicity of binding sites for biotin or biotin derivatives, wherein said fused gene is capable of expressing a fused protein in vivo when the gene is inserted into a suitable expression vector and introduced into a suitable host cell. This fused gene may be used to produce labeled, chemically modified proteins in vivo and to isolate proteins when one knows only the sequence of the gene encoding the protein.

In accordance with the present invention a method for producing a labeled protein of interest in vivo comprises the following steps:

(a) ligating the DNA encoding the protein of interest to the DNA encoding streptavidin of the present invention thereby producing a fused gene;

(b) inserting the fused gene into a suitable expression vector;

(c) introducing the expression vector into a suitable host cell under appropriate conditions permitting expression of the fused gene and production of the fused protein;

(d) isolating the fused protein;

(e) incubating the fused protein with biotin or a biotin derivative in vitro, thereby producing a fused protein-biotin complex wherein the biotin or biotin derivative is bound to the streptavidin portion of the fused protein; and (f) introducing the fused protein-biotin complex into the host cell of step (c) under appropriate conditions that allow the biotin or biotin derivative to bind with unlabeled fused protein produced by the host cell, thereby producing a labeled or chemically modified protein of interest in vivo.

A method of isolating a protein of interest comprises the following steps:

(a) ligating the DNA encoding the protein of interest to the DNA encoding streptavidin of the present invention thereby producing a fused gene;

(b) inserting the fused gene into a suitable expression vector;

(c) introducing the expression vector into a suitable host cell under appropriate conditions permitting expression of the fused gene and production of the fused protein;

(d) contacting the fused protein with biotin or a biotin derivative under conditions permitting the biotin or biotin derivative to bind to the streptavidin portion of the fused protein, thereby producing a fused protein-streptavidin-biotin complex; and (e) isolating the complex and thereby isolating the protein of interest.

BRIEF DESCRIPTION OF THE FIGURES

FIG. 1 depicts the amino-terminal amino acid sequence of streptavidIn and the nucleotide sequences of two oligonucleotide probes used for the isolation of the streptavidin gene. (N: A, G, C and U or T).

FIG. 3 depicts the nucleotide sequence of the gene for streptavidin and the restriction sites used for modification of the 5' and 3' regions. Above the nucleotide sequence is the amino acid sequence of the streptavidin protein. The amino acids of the signal peptide are indicated with negative numbers.

FIG. 4 depicts the amino acid sequence comparison of streptavidIn and avidin. Identical residues are enclosed by solid lines and chemically similar residues by broken lines. Both sequences were aligned to give maximum homology. (Heterogeneity in residue number 34 of avidin has been reported (25); Ile or Thr is present in this position).

FIG. 5 depicts the comparison of predicted secondary structures of streptavidin and avidin. The sequences have been aligned as in FIG. 4.: alpha-helix, B: beta-strand, T: turn. (The final 20 C-terminal amino acids of streptavidin were not analyzed).

DETAILED DESCRIPTION OF THE INVENTION

Figure 2:
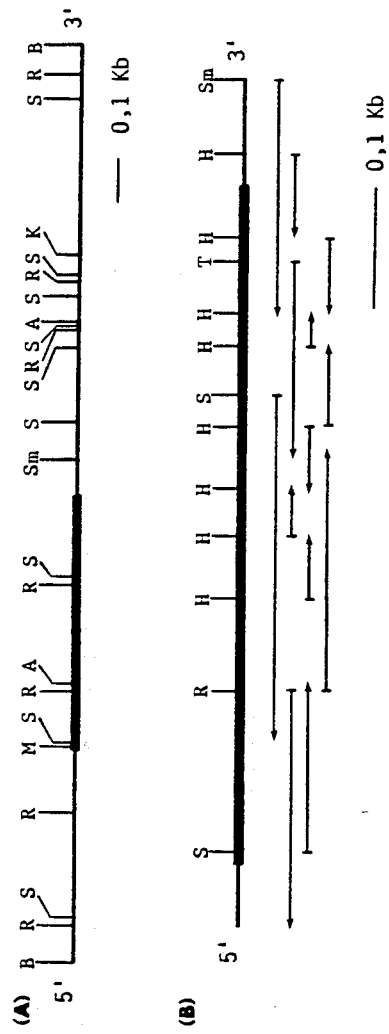
FIG. 2 depicts the partial restriction map of the cloned 2 kb-fragment (A) and strategy used for DNA sequence analysis (B). The arrows indicate the direction and extent of the fragments sequenced. The shaded region corresponds to the coding sequence. (B: BamHI, R: RsaI, S: Sau3AI, M: MstI, A: AluI, Sm: SmaI, K: KpnI, H: HaeIII, T: TacI).

The present invention provides isolated DNA which encodes streptavidin. The DNA has been isolated as a fragment 2 kb in length, is derived from a restriction endonuclease digestion of the chromosomal DNA of *Streptomyces avidinii* and has the nucleic acid sequence identified in FIG. 3. The 2 kb fragment contains the entire region encoding the streptavidin polypeptide, a region encoding a signal peptide and the flanking region DNA which occurs naturally at the 3' and 5' ends of the coding region.

A recombinant cloning vehicle is also provided which comprises cloning vehicle DNA and the 2 kb segment of DNA encoding the polypeptide streptavidin, wherein the 2 kb segment is derived from the chromosomal DNA of *Streptomyces avidinii*, said cloning vehicle DNA being characterized by the presence of a first and a second restriction enzyme site and the 2 kb segment being inserted into said sites. The 2 kb segment contains the entire region encoding the polypeptide streptavidin, a region encoding a signal peptide, and the flanking region DNA which occurs naturally at the 3' and 5' ends of the coding region.

The cloning vehicle of the present invention may be of bacterial or viral origin. A suitable plasmid cloning vehicle is a pUC plasmid. A suitable phage cloning vehicle is the phage M13.

The recombinant cloning vehicle of the present invention has been inserted into a bacterial host cell. A suitable bacterial host cell is *E. coli*. A genetically engineered *E. coli* host cell containing the recombinant cloning vehicle of the present invention has been prepared and is designated JM83 (ATCC Accession No. 53307). A method of preparing streptavidin comprises cultivating a genetically engineered host cell of the present invention under suitable conditions permitting expression of the streptavidin gene and recovering the streptavidin so produced.

Substantially pure, biotIn free streptavidin produced by recombinant DNA techniques comprises four identical polypeptide subunits, each having a molecular weight of about 16,500 daltons and a multiplicity of free biotin binding sites. The streptavidin subunits each have the amino acid sequence of FIG. 3. The streptavidin of the present invention has a majority of its amino acids in the beta-conformation.

The preferred number of free biotin binding sites is four. The free biotin binding sites are adjacent to lysine residues which are at positions 80 and 121. The free biotin binding sites comprise critical tryptophan binding residues wherein the critical tryptophan binding residues are at positions 21, 79 or 120, and wherein the critical tryptophan binding residues are adjacent to lysine residues.

The polypeptide streptavidin may be prepared with an amino terminal label which is susceptible to proteolytic cleavage. The amino terminal label may be a radiolabel or a fluorescent label. Alternatively, the polypeptide streptavidin may be prepared with a carboxy terminal label susceptible to proteolytic cleavage, wherein the carboxy terminal label is a radiolabel or a fluorescent label. The carboxy terminal label may also be an identifiable cysteine.

The present invention also provides a fused gene which comprises a first DNA fragment encoding a target protein of interest fused to a second DNA fragment encoding streptavidin, said streptavidin having a multiplicity of binding sites for biotin or a biotin derivative, and wherein the fused gene is capable of expressing a fused protein in vivo when the gene is inserted into a suitable expression vector and introduced into a suitable host cell. The fused gene may have at its 5' end either the first DNA fragment encoding the target protein or the second DNA fragment encoding streptavidin. The DNA fragment encoding streptavidin of the fused gene is 2 kb in length, is derived from a restriction endonuclease digestion of the chromosomal DNA of *Streptomyces avidinii* and has the nucleic acid sequence of FIG. 3. The 2 kb fragment contains the entire region encoding the polypeptide streptavidin, a region encoding a signal peptide and the flanking region DNA which occurs naturally at the 3' and 5' ends of the coding region.

In one embodiment of the invention, the first DNA fragment is the gene encoding the human light density lipoprotein (LDL) receptor. Such a fused gene expresses a protein which consists of streptavidin at the N-terminal region of the fused protein and the LDL receptor protein at the C-terminal region of the fused protein when the fused gene is inserted into a suitable expression vector and introduced into a suitable host cell. The fused gene may be cloned into a mammalian expression vector which may then used to transfect a mammalian host cell with the fused gene. A preferred mammalian host cell is an NIH 3T3 cell.

An expression vector capable of expressing the fused gene of the present invention, when introduced into a suitable host cell comprises, suitable carrier DNA and the fused DNA fragments of the present invention. Suitable carrier DNA may be plasmid or phage DNA. The expression vector may be a bacterial or eucaryotic expression vector. Suitable bacterial expression vectors comprise a double-stranded DNA molecule, which includes in 5' to 3' order the following:

a DNA sequence which contains either a promoter or a promoter and operator;
a DNA sequence which contains a ribosomal binding site for rendering the mRNA of the desired gene capable of binding to ribosomes within the host cell;
an ATG initiation codon;
a restriction enzyme site for inserting a desired gene into the vector in phase with the ATG initiation codon;
a DNA sequence which contains an origin of replication from a bacterial plasmid capable of autonomous replication in the host cell; and
a DNA sequence which contains a gene associated with a selectable or identifiabl phenotypic trait and which is manifested when the vector is present in the host cell.

Also provided is a fused protein encoded by the fused gene of the present invention, wherein a target protein of interest is fused to streptavidin, wherein the streptavidin has a multiplicity of binding sites for biotin or a biotin derivative. In one embodiment, the target protein is the human LDL receptor. In another embodiment, the target protein is a monoclonal antibody. In a further embodiment, the biotin derivative is a fluorescent biotin.

A method for producing a labeled protein of interest in vivo comprises the following steps:
(a) ligating the DNA encoding the protein of interest to the DNA encoding streptavidin of the present invention thereby producing a fused gene;
(b) inserting the fused gene into a suitable expression vector;
(c) introducing the expression vector into a suitable host cell under appropriate conditions permitting expression of the fused gene and production of the fused protein;
(d) isolating the fused protein;
(e) incubating the fused protein with biotin or a biotin derivative in vitro, thereby producing a fused protein-biotin complex wherein the biotin or biotin derivative is bound to the streptavidin portion of the fused protein; and
(f) introducing the fused protein-biotin complex into the host cell of step (c) under appropriate conditions that allow the biotin or biotin derivative to bind with unlabeled fused protein produced by the host cell, thereby producing a labeled or chemically modified protein of interest in vivo.

A method of isolating a protein of interest comprises the following steps:
(a) ligating the DNA encoding the protein of interest to the DNA encoding streptavidin of the present invention thereby producing a fused gene;
(b) inserting the fused gene into a suitable expression vector;
(c) introducing the expression vector into a suitable host cell under appropriate conditions permitting expression of the fused gene and production of the fused protein;
(d) contacting the fused protein with biotin or a biotin derivative under conditions permitting the biotin or biotin derivative to bind to the streptavidin portion of the fused protein, thereby producing a fused protein-streptavidin-biotin complex; and
(e) isolating the complex and thereby isolating the protein of interest.

The present invention provides a method of generating labeled proteins in vivo and a method of isolating a target protein knowing only the nucleotide sequence of its gene. The basic concept is to fuse the gene encoding a protein (target) of interest to the gene encoding another protein (marker) which has a binding site having a high affinity for a specific ligand, wherein a protein fusion is produced when the gene is expressed in vivo. In this manner the ligand binding site can be used to create a chemically labeled protein in vivo by the addition of appropriate modified ligands. The target protein can be any protein of interest. For example, any protein of bacterial or viral origin can be a target protein if the nucleotide structure of the gene encoding the protein is known. In the present invention the marker protein is streptavidin. However, aequorin or any other protein having a high affinity ligand binding site may be a suitable marker protein.

Streptavidin binds biotin and many chemically modified biotins are available, such as fluorescent biotins, which also bind to streptavidin. Thus a gene fusion with the streptavidin gene allows the in vivo production of fused proteins which may be specifically labeled with a fluorphore whenever desired, in vivo or in vitro.

The present invention contemplates the production of labeled monoclonal antibodies. Such monoclonal antibodies would have a unique attachment site for a fluorescent dye. No covalent in vitro modification would be required. There would be no batch to batch variation in the product. Also, the present invention contemplates fusion labeled proteins to facilitate the isolation of rare or unstable proteins by making use of existing biotin-streptavidin affinity separation schemes.

It is desirable to be able to label and detect small amounts of interesting proteins within living cells. The methods of the present invention enable the isolation of proteins knowing only the DNA sequence encoding them. The implications and applications are many. For example, in cells producing a labeled oncogene product, the cellular location of the oncogene product may be analyzed using the methods of the present invention. For specific genes which are turned on in only a few cells, these cells can be isolated and identified by FACS.

A number of small proteins are easily detected in vivo either because they are chemiluminescent when the correct cofactor is added or because they bind a small molecule with great specificity and affinity. The genes for these proteins may be cloned and placed into vectors that promote strong expression in mammalian cells. This system may be used to confirm the ability to detect the protein by the addition of cofactors or labeled small molecules. The vector may be altered to facilitate the construction of protein fusions. Inserting a gene for a cellular protein into the vector will result in a gene fusion. The vector containing fused genes may be reinserted into cells and the properties, location, extent, and control of the in vivo synthesized fusion protein characterized. Where suitable mutants exist one will also be able to assess whether the protein fusion retains normal function. If necessary, a short collagen bridge may be constructed between the cellular protein and the labeled protein.

EXAMPLE 1

Isolation and Characterization of A Genomic DNA Clone Encoding Streptavidin

Materials and Methods

Enzymes and other reagents. All enzymes and chemicals used were from Bethesda Research Laboratories, New England Biolabs, Boehring Mannheim Biochemicals or Pharmacia P-L Biochemicals. Radiochemicals were from New England Nuclear. Streptavidin, pUC8 and M13 were supplied by Bethesda Research Laboratories.

Amino acid sequence and amino acid analysis. Analysis by SDS-polyacrylamide gel electrophoresis of the preparation of streptavidin used showed, in addition to a main protein band, some material of lower molecular weight, possibly a degradation product of the protein. In order to obtain a pure component for amino acid sequence analysis, the preparation of streptavidin was electrophoresed in a preparative 15% slab SDS-polyacrylamide gel (9) and the main and higher molecular weight protein band was purified from the gel. Visualization of the protein bands, elution and SDS elimination were carried out essentially according to Hager and Burgess (10). Amino terminal sequence analysis of the protein was performed using a Beckman 890B automatic sequencer. The identification of amino acids was carried out by HPLC (11). For amino acid analysis, the gel-purified protein was hydrolyzed with 6N HCl in the presence of beta-mercaptoethanol (1:1000) at 110° C. under vacuum for 24 h, and the hydrolysate was analyzed on a Beckman 121MB amino acid analyzer.

Synthesis, purification and labeling of oligonucleotides. Oligonucleotide mixtures were synthesized by the solid-phase phosphite triester method using an Applied Biologicals DNA/RNA synthesizer (12).

The oligonucleotides were purified by preparative polyacrylamide gel electrophoresis on a 15% sequencing gel. The oligonucleotide probes used for the isolation of the streptavidin gene are depicted in FIG. 1.

Purified oligonucleotides were labelled at the 5' end with gamma-[$^{32}$P]ATP (4,000–6,000 Ci/mmol) and polynucleotide kinase. Unincorporated ATP was removed by chromatography on DEAE-cellulose (13).

Construction of the genomic library from *Streptomyces avidinii*. Purified chromosomal DNA from *Streptomyces avidinii* was partially digested with MboI and the DNA fragments ranging between 6–19 kb were purified by agarose gel electrophoresis. Charon 30 DNA (14) was digested to completion with BamHI, the arms isolated by agarose gel electrophoresis and then ligated with the DNA fragments of *Streptomyces avidinii* using T4 DNA ligase. The recombinant DNA was packaged in vitro into viable bacteriophage particles according to Maniatis et al. (15).

Screening of DNA clones. *E. coli* LE 392 cells were infected with the recombinant phages, plated in NZYCM-soft agarose on NZYCM agar plates and grown at 37° C. Two plates containing approximately $8 \times 10^3$ phages each were used for the screening. Three replica plates were prepared for hybridization according to Benton and Davis (16). Filters were pre-hybridized in 75 mM Tris-HCl pH 8, 100 mM sodium phosphate pH 6.5, 750 mM NaCl, 5 mM EDTA, 1% SDS, $10 \times$ Denhardt and 100 micrograms per ml of denatured salmon sperm DNA for 3 h at 25° C.

Hybridization was done in the same solution in the presence of 4 ng/ml of labelled probe (Stv14, see FIG. 1) at a specific activity of $10^8$–$10^9$ cpm per microgram of oligonucleotide. Filters were hybridized at 25°, 28° and 31° C. (one replica at each temperature) for 30–36 h then washed at 25° C. for 45 min with three changes of 250 ml of the same solution used for pre-hybridization except that Denhardt and DNA were omited. Filters were blotted dry and exposed to Kodax XR5 X-ray film with an intensifying screen.

DNA sequence analysis. Restriction fragments of the gene were subcloned into M13, mp18 and mp19 (17) and sequenced by the dideoxy chain termination method (18).

Figure 6:
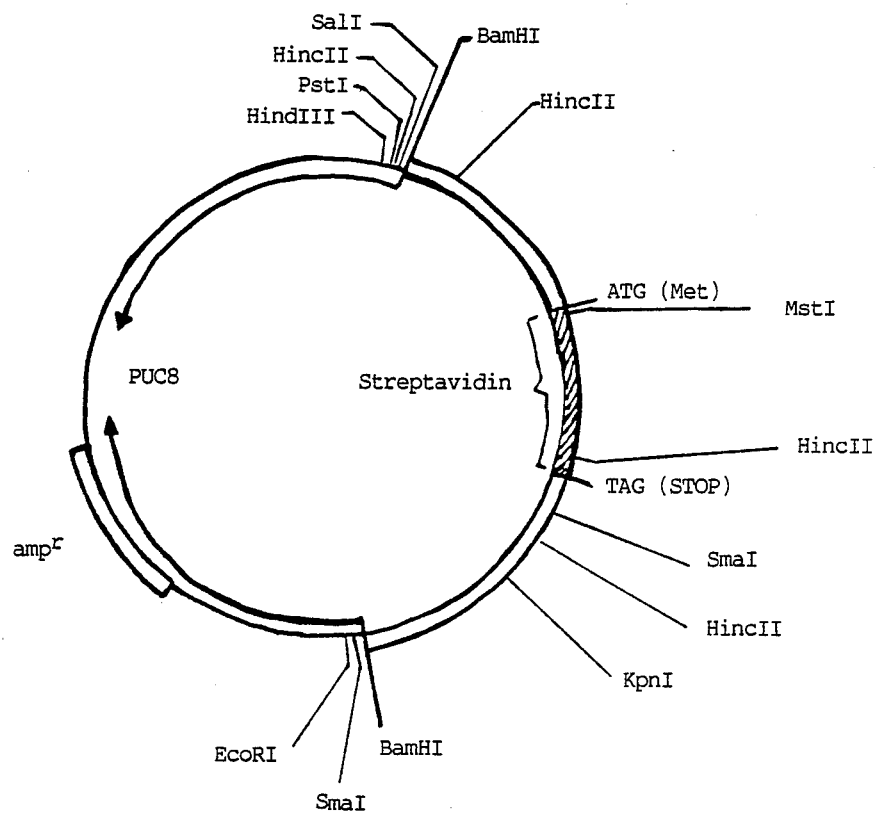
FIG. 6 depicts the restriction map of plasmid pUC8-S2.

Additionally, the streptavidin gene (2 kb fragment) was subcloned into the plasmid pUC8, resulting in the formation of a new plasmid designated pUC8-S2. A restriction map of the plasmid pUC8-S2 is depicted in FIG. 6.

The plasmid pUC8-S2 was used to transform *E. coli* strain K-12 resulting in new strain JM83. *E. coli* strain JM83, containing the plasmid pUC8-S2, has been deposited in the American Type Culture Collection, Rockville, Md., as ATCC No. 53307. This deposit was made pursuant to the Budapest Treaty On The International Recognition Of The Deposit Of Microorganisms For the Purposes of Patent Procedure.

Secondary structure prediction method. Computer programs have been developed that compare the amino acid sequences of proteins to a series of sequence patterns that have been shown to be characteristic of secondary structure elements inproteins of known tertiary structure (19–21). These patterns have been found to be approximately 90% accurate in identifying the turns that separate helices and beta strands (20). The patterns used to evaluate helical and beta propensities were taken from a study of alpha/beta proteins (19) augmented with other characteristics of all-helical and all-beta proteins (20). These patterns are clearly more reliable (ca. 70% correct) than the turn finding procedure. Extension of the methods to groups of sequences known to be closely related (e.g. myoglobins and immunoglobulins) did not degrade the reliability of the method (19).

Results and Discussion

Amino acid sequence of streptavidin. Amino-terminal amino acid analysis of a commercial preparation of streptavidin indicated the presence of both alanine and aspartic acid in the first cycle of Edman degradation of the protein. This heterogeneity can be explained by the fact that when this preparation was examined by SDS-polyacrylamide gel electrophoresis, two main protein bands with an approximate molecular weight of 17.5 and 15.5 kd were observed. The higher molecular weight band accounted for 60–70% of the total stained protein material present in the gel. To determine the amino acid sequence, the 17.5 kd-polypeptide chain was gel purified as previously described in the Materials and Methods section. FIG. 1 shows the amino acid sequence obtained for the 40 amino-terminal residues of the protein.

Isolation of the clone containing the streptavidin gene.

The approach used for the isolation of the clone containing the streptavidin gene was to screen a genomic library of Streptomyces avidinii with a mixture of 16 oligonucleotides, that represent all possible codon combinations for a small portion of the amino acid sequence of streptavidin (FIG. 1). One specific probe 14 nucleotides long was designated Stv14.

Several clones, which remained positive at the three temperatures of hybridization used (see Materials and Methods) were isolated. In order to confirm the presence of the desired clone, purified DNA from each presumptive positive clone was cut with BamHI, the DNA fragments separated by agarose gel electrophoresis and analyzed by Southern blot technique (22). In addition to Stv14, another probe, Stv11 (FIG. 1) which was derived from a different part of the amino acid sequence, was used. Both probes, Stv14 and Stv11, hybridized specifically to a single fragment of approximately 2 kb.

The Southern blot analysis of the cloned DNA for streptavidin was accomplished by digesting the DNA from a positive clone with BamHI. The DNA fragments were subjected to electrophoresis on a 0.9% agarose gel, visualized by staining with ethidium bromide, and transfered to nitrocellulose filter paper by the standard Southern blotting technique (22). Duplicate blots were hybridized with 20 ng/ml of $^{32}$P-labeled Stv14 or Stv11 at 27° C. for 20 hours. The hybridization solution and the washing conditions were the same used for the screening of the library.

Nucleotide sequence analysis and amino acid sequence.

In order to identify the region containing the complementary sequence of the probe, the 2 kb-fragment was cut with Sau3AI, subcloned into BamHI-cut M13 and the recombinants screened with $^{32}$P-labelled Stv14 probe. The DNA sequence obtained from isolated positive clones showed the presence of part of the coding region of the gene and the sequence complementary to both probes. To localize this sequence within the 2 kb-fragment, a partial restrictionmap of the 2 kb-fragment was prepared using the method of Smith and Birnstiel (23). In order to obtain the complete nucleotide sequence of the gene, appropriate overlapping fragments were subcloned into M13 and sequenced. FIG. 2 shows the partial restriction map of the 2 kb-fragment and the strategy used to sequence the streptavidin gene.

The complete nucleotide sequence of the streptavidin gene along with the amino acid sequence is shown in FIG. 3. The amino acid sequence of residues 1 to 40 is in perfect coincidence with that obtained from the protein sequence shown in FIG. 1. The amino-terminal amino acid of the protein isolated in vitro is aspartic acid, thus residues −24 to −1 must be post-translationally removed to yield this mature protein. The extra 24 amino acids show common characteristics with those signal peptides present in the genes of most secreted proteins (24). This finding is in agreement with the fact that streptavidin has been described as a secreted protein (1). After amino-terminal processing the mature protein contains 159 amino acids and has a calculated molecular weight of 16,500 daltons, which is in close agreement with the value of approximately 17,500 daltons found for each streptavidin subunit by SDS-polyacrylamide gel electrophoresis.

A comparison of the following three different determinations of the amino acid composition of streptavidin is shown in Table 1: the amino acid composition as deduced from the nucleotide sequence of the streptavidin gene, the amino acid composition derived from analysis of the gel-purified protein and a previously reported amino acid composition (4).

TABLE 1

Amino acid composition of streptavidin

Residues per subunit

| Amino acid | Amino Acid[a] composition deduced from nucleotide sequence | Amino acid[b] analysis (this work) | Amino acid[c] analysis (earlier work) |
| --- | --- | --- | --- |
| Lys | 8 | 8.7 | 4 |
| His | 2 | 2.6 | 2 |
| Arg | 4 | 3.0 | 4 |
| Asp | 8 | 18.0* | 12* |
| Asn | 10 | 18.0* | 12* |
| Thr | 19 | 18.3 | 19 |
| Ser | 14 | 13.0 | 10 |
| Glu | 5 | 11.3* | 9* |
| Gln | 6 | 11.3 | 9* |
| Pro | 4 | 3.7 | 2 |
| Gly | 18 | 20.6 | 17 |
| Ala | 25 | 25.0 | 17 |
| Cys | 0 | 0 | 0 |
| Val | 10 | 10.1 | 7 |
| Met | 0 | 0 | 0 |
| Ile | 4 | 4.0 | 3 |
| Leu | 8 | 8.5 | 8 |
| Tyr | 6 | 6.1 | 6 |
| Phe | 2 | 2.1 | 2 |
| Trp | 6 | 4.0# | 8 |

[a]The composition of the mature protein after N-terminal processing is given.
[b]The values were calculated from the amino acid analysis of the gel-purified protein.
[c]The values were taken from reference (4).
*Because acid hydrolysis of proteins results in deamination of asparagine and glutamine, these amino acids are not distinguished from aspartate and glutamate.
Tryptophan recovery was low since HCl hydrolysis was employed (addition of Beta-mercaptoethanol permitted some recovery of tryptophan).

The values obtained from nucleotide sequencing are in good agreement with those obtained from amino acid analysis of the gel-purified protein within the error of amino acid analysis. The previously reported number of residues per streptavidin subunit was calculated assuming a total of 130 residues for the protein (4). Comparison of these values with those obtained from the nucleotide sequence shows differences in several amino acids. This discrepancy cannot be explained by an underestimation in the total number of residues since some differences persist and others appear after correction of the reported values for a total of 159 amino acids. It is interesting to point out that identical or similar values are found for those amino acids that are absent or rarely present in the N- or C-terminal region of the processed streptavidin. In addition to this observation, a different commercial preparation of streptavidin showed a lower and variable molecular weight than the polypeptide that was used to determine the amino acid sequence. This suggests that the N-and/or C-terminal regions of the protein may be particularly susceptible to proteolytic degradation. Calculations show that the 10–12 N-terminal residues plus the 19–21 C-terminal residues account, approximately, for the discrepancy found in the amino acid content shown in Table 1. Therefore, it is believed that the previously reported amino acid analysis was probably obtained from a partially degraded streptavidin.

Primary and secondary structure comparison of streptavidin and avidin. FIG. 4 shows the amino acid sequence of streptavidin compared with that of avidin (25), the biotin-binding protein from chicken egg-white. Streptavidin has 159 amino acids compared with 128 for avidin. Several regions of extensive homology were found between both proteins. Of particular interest is the homology around and including tryptophans 21, 79 and 120 of streptavidin. In avidin, the corresponding tryptophans 10, 70 and 110 are protected by biotin from oxidizing agents suggesting that these residues are implicated in the biotin-binding site of the protein (4). Besides this, a unique NH$_2$-group, probably one of the three lysine residues (9, 71 and 111) which are adjacent to the tryptophans, has been found to be important for the biotin-binding activity of avidin (4). In streptavidin, two of these three lysines are conserved as lysine residues (80 and 121) also next to tryptophans.

Secondary structures were calculated for both proteins using algorithms that predict conformation from amino acid sequence (19–21). FIG. 5 shows the residues at which alpha-helical, beta-strand or turn features are centered. Both proteins show a clear structural homology with a high preponderance of beta-structure. The alternating hydrophobic, hydrophilic pattern for most of the suggested beta-strands is consistent with a folded beta-sheet or beta-barrel geometry (26). The overall composition pattern of both sequences suggests that both proteins fall in the family of "all beta" proteins (27). The list of turns shown in FIG. 5 is incomplete but there is a good probability (19) that the assigned ones are correct. The extent and exact location of beta-structure is more difficult to predict. On the other hand it is clear there is little, if any, alpha-helix in both proteins. The best change for finding alpha-helices is in the N-terminal region of streptavidin and the C-terminal region in both proteins.

In agreement with these predictions, avidin has been found to have a content of 55% of beta-structure and 5% of alpha-helix as determined by Raman spectroscopy (28).

EXAMPLE 2

Expression of a Streptavidin-Human-LDL Receptor Gene Fusion In Mammalian Cells A gene construction fusing the streptavidIn gene to the human low density lipoprotein (LDL) receptor gene so that their reading frames remained in phase was made in such a way that the streptavidin gene was located at the 5' end of the gene fusion and the human LDL receptor gene at the 3' end. The expressed protein consists of streptavidin at the N-terminal region and the LDL receptor at the C-terminal region of the hybrid protein.

In order to fuse both genes, 11 codons of the 3' region of the streptavidin gene were deleted in vitro. The region of the LDL receptor gene used in the fusion was the region that codes for 159 amino acids of the C-terminal region of the protein. In the native receptor this region comprises a short extracellular tail (88 amino acids), the membrane spanning region (22 amino acids) and the intracellular domain (49 amino acids).

Modification of the 5' and 3' region of the streptavidin gene. The nucleotide sequence of the streprtavidin (STV) gene and the restriction sites used for the modification of the 5' and 3' region are shown in FIG. 3.

Figure 7:
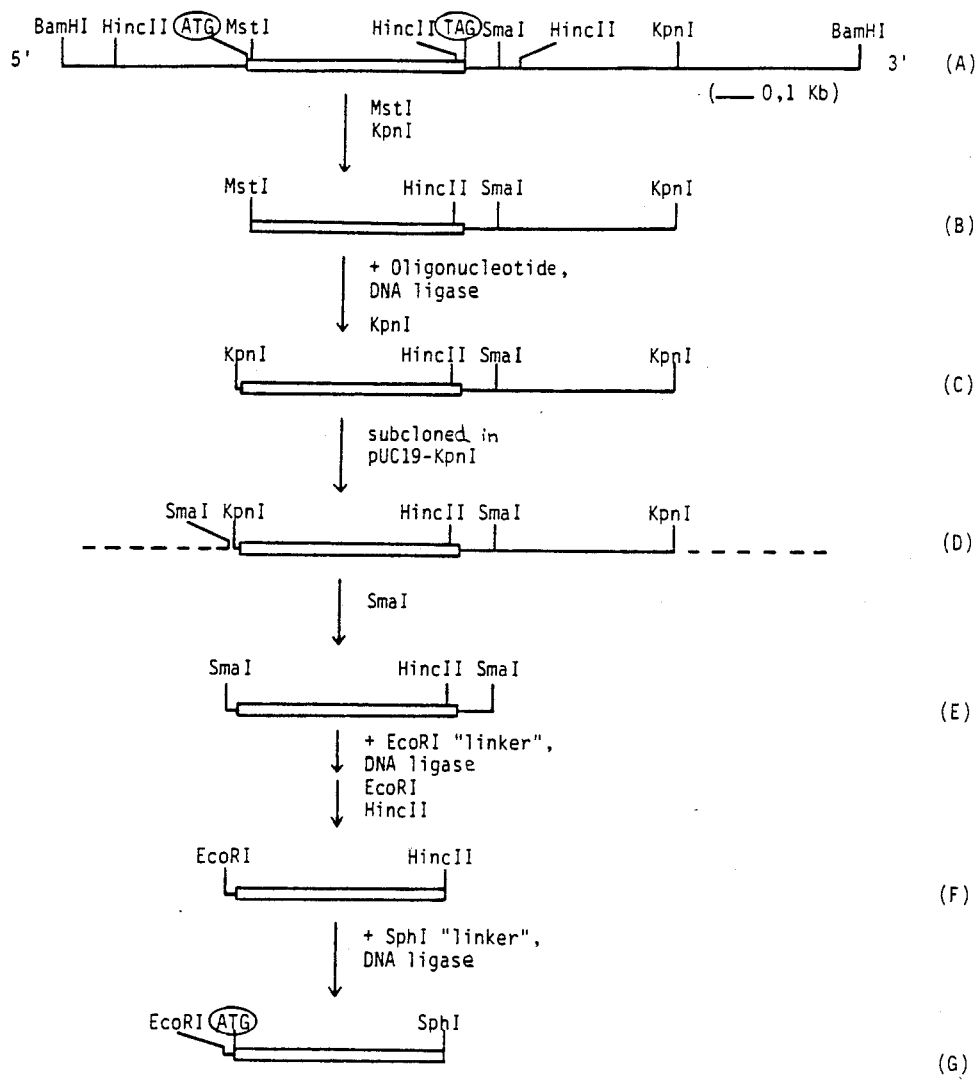
FIG. 7 shows the steps and reactions carried out for the modification of the 5' region of the streptavidin gene.

FIG. 7 shows the reactions carried out for the modification of the 5' region of the STV gene. A 2 kb-fragment containing the STV gene (FIG. 7, Step A) was treated with MstI and KpnI and the resulting fragment containing the STV gene purified (FIG. 7, Step B). This fragment was modified by the addition of a synthetic oligonucleotide containing the sequence of the STV gene eliminated by MstI treatment as well as a restriction site for the enzyme KpnI placed immediately upstream of the initiation codon. The nucleotide sequence in the site of this modification is depicted below:

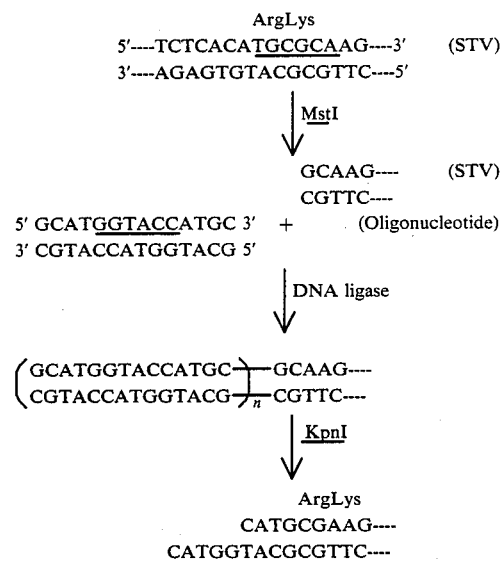

Autoradiography of a sequencing gel verified the sequence of the modified region.

The modified fragment (FIG. 7, step C) was subcloned into pUC19 (FIG. step D), treated with SmaI and the fragment containing the STV gene purified (FIG. 7, step E). After modification of both ends with EcoRI linkers the fragment was treated with HincII (FIG. 7, step F) and again modified by ligation of SphI linkers (FIG. 7, step G). The nucleotide sequence in the site of the modification of step G from FIG. 7 is:

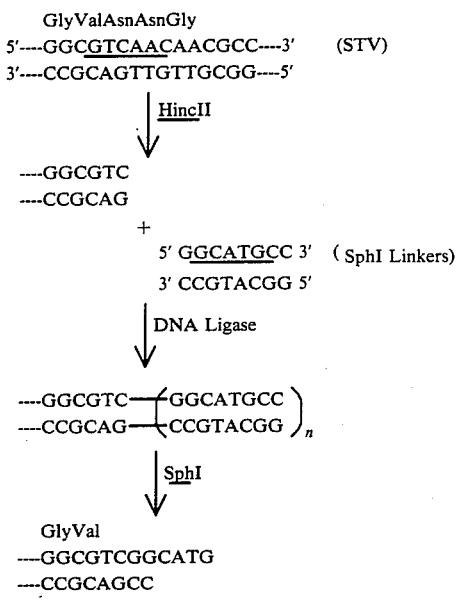

```
GlyValAsnAsnGly
5'----GGCGTCAACAACGCC----3'     (STV)
3'----CCGCAGTTGTTGCGG----5'
          |
          | HincII
          v
----GGCGTC
----CCGCAG
          +
      5' GGCATGCC 3'   ( SphI Linkers)
      3' CCGTACGG 5'
          |
          | DNA Ligase
          v
----GGCGTC--(GGCATGCC )
----CCGCAG--(CCGTACGG )n
          |
          | SphI
          v
GlyVal
----GGCGTCGGCATG
----CCGCAGCC
```

Fusion of the STV gene with the LDL receptor gene. The restriction map and nucleotide sequence of the human LDL receptor gene has been previously determined (29). The restriction sites used for the fusion were the EcoRI site, located at about 0.7 kb, the SphI site, located at about 2.1 kb, and the SmaI site, located at about 2.8 kb.

Figure 8:
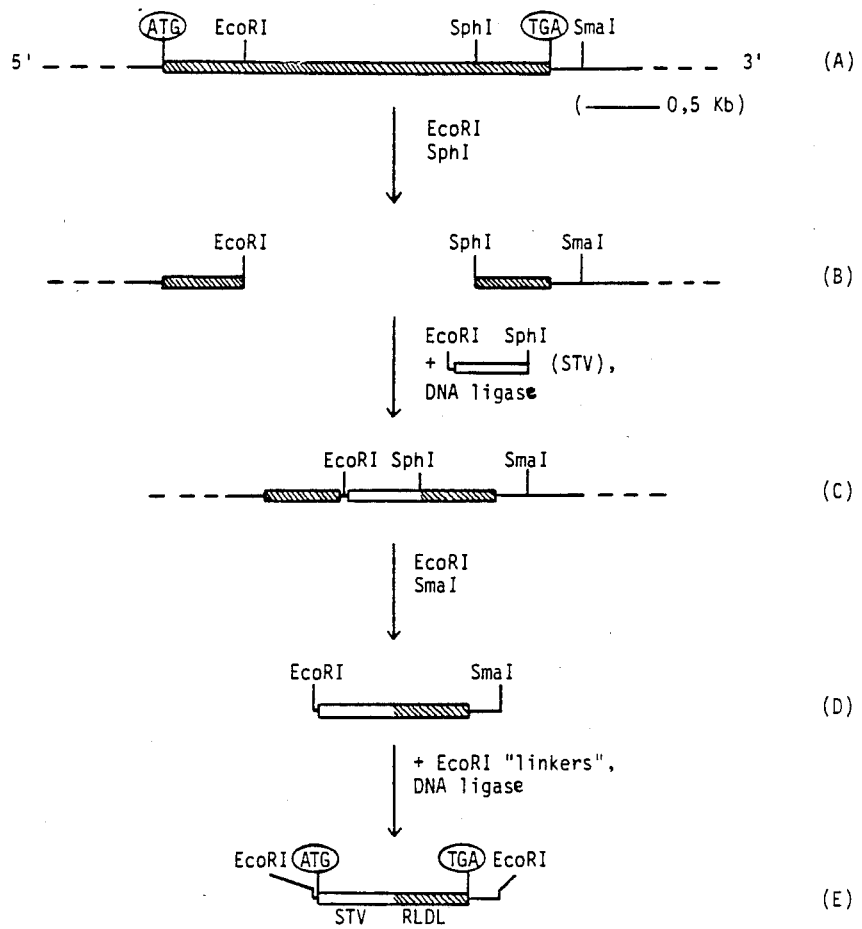
FIG. 8 shows the reactions and steps carried out in the fusion of the streptavidin gene and the human LDL receptor gene.

FIG. 8 shows the reactions carried out to fuse both genes. The plasmid containing the LDL receptor gene (FIG. 8, step A) was treated with EcoRI and SphI. The fragment shown in FIG. 8, step B was purified and used to insert the STV gene (FIG. 8, step C). The nucleotide sequence in the fusion site of both genes is:

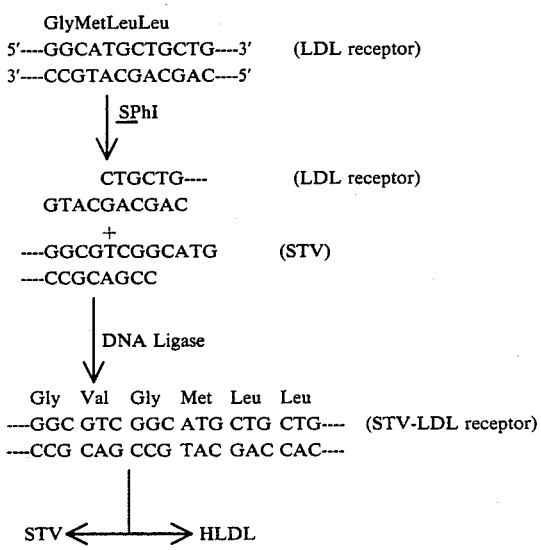

```
GlyMetLeuLeu
5'----GGCATGCTGCTG----3'    (LDL receptor)
3'----CCGTACGACGAC----5'
        |
        | SPhI
        v
      CTGCTG----             (LDL receptor)
GTACGACGAC
        +
----GGCGTCGGCATG            (STV)
----CCGCAGCC
        |
        | DNA Ligase
        v
Gly  Val  Gly  Met  Leu  Leu
----GGC GTC GGC ATG CTG CTG----   (STV-LDL receptor)
----CCG CAG CCG TAC GAC CAC----
               |
STV <----------+----------> HLDL
```

This nucleotide sequence was confirmed by autoradiography.

After recovering the STV-LDL receptor fragment by treatment with EcoRI and SmaI (FIG. 8, Step D), the fragment was modified by the addition of EcoRI linkers (FIG. 8, Step E).

The modified fragment, or fused gene, was subcloned into pMV7, a mammalian expression vector and the resulting plasmid used to transfect NIH 3T3 cells using the calcium phosphate precipitation method (31). Colonies of cells resistant to the antibiotic G418 were examined for the expression of STV by means of the binding of red blood cells coupled to biotinylated bovine serum albumin. After washing off the excess of red cells some of the colonies had bound red cells, which is evidence that streptavidin fusion was expressed and transported to the cell membrane.

References

1. Chaiet, L., Miller, T. W., Tausing, F. and Wolf, F. J. (1963), Antimicrob. Agents Chemother. 3, 28–32.
2. Chaiet L. and Wolf, F. J. (1964), Arch. Biochem. Biophys. 106, 1-5.
3. Green, N. M. (1963), Biochem. J. 89, 585–589.
4. Green, N. M. (1975) Advances in Protein Chemistry 29, 85–133.
5. Bayer, E. A. and Wilcheck, M. (1980), Methods of Biochemical Analysis 26, 1–46.
6. Langer, R. L., Waldrop, A. A. and Ward, D. C. (1981), Proc. Natl. Acad. Sci. USA 78, 6633–6637.
7. Haeuptle, M. -T., Aubert, M. L., Djiane, J. -P. and Kraehenbuhl, J. (1983), J. Biol. Chem. 258, 305–314.
8. Hsu, S. -M. and Raine, L. (1981), J. Histochem. Cytochem. 29, 1349–1353.
9. Laemmli, U. (1970), Nature 227, 680–685.
10. Hager, D. A. and Burgess, R. R. (1980), Anal. Biochem. 109, 76–86.
11. Zimmerman, C. L., Apella, E. and Pisano J. J. (1973), Anal. Biochem. 77, 569–573.
12. Urbina, G. A., Sathe, G. M., Liu, W., Guillen, M. F., Duck, P. D., Bender, R. and Ogilvie, K. K. (1981), Science 214, 270–274.
13. Wallace, R. B. (1981), Gene 16, 21–26.
14. Rimm, D. V., Horness, D., Kucera, J. and Blattner, F. R. (1980), Gene 12, 301–309.
15. Maniatis, T., Fritch, E. F. and Sambrook, J. (1982), Molecular Cloning. (Cold Spring Harbor, New York: Cold Spring Harbor Laboratory).
16. Benton, W. D. and Davis, R. W. (1977), Science 196, 180–182.
17. Sanger, F., Nicklen, S. and Coulson, A. R. (1977), Proc. Natl. Acad. Sci. USA 74, 5463–5467.
18. Vieira, J. and Messing, J. (1982), Gene 19, 259–268.
19. Cohen, F. E., Abarbanel, R. M., Kuntz, I. D. and Fletterick, R. J. (1983), Biochemistry 22, 4894–4904.
20. Cohen, F. E., Abarbanel, R. M., Kuntz, I. D. and Fletterick, R. J. (1985), Biochemistry (in press).
21. Abarbanel, R. M. (1984), PhD thesis, University of California.
22. Southern, E. M. (1975), J. Mol. Biol. 98, 503–517.
23. Smith, H. O. and Birnstiel, M. L. (1976), Nucleic Acids Res. 3, 2387–2398.
24. Kreil, G. (1981), Ann. Rev. Biochem. 50, 317–348.
25. De Lange, R. J. and Huang, T. -S. (1971), J. Biol. Chem. 246, 698–709.
26. Richardson, J. S. (1981), Adv. Protein Chem. 34, 167–339.
27. Sheridan, R. Dixon, J. S., Venkataraghavan, R., Scott, K. and Kuntz, I. D. (1985), Biopolymers (in press).
28. Honzatko, R. B. and Williams, R. W. (1982), Biochemistry 21, 6201–6205.
29. Yamamoto et al. (1984), Cell 39: 27–38.
30. Maddon et al. (1985), Cell 42: 93–104.
31. Wigler et al. (1978), Cell 14: 725–731.

What is claimed is:

1. An isolated DNA molecule encoding streptavidin and comprising the nucleic acid coding sequence set forth in FIG. 3.

2. A recombinant cloning vehicle which comprises a cloning vehicle DNA and the DNA of claim 1.

3. The cloning vehicle of claim 2, comprising the entire region coding for the polypeptide streptavidin, a region encoding a signal peptide and the flanking region DNA which occurs naturally at the 3' and 5' ends of the coding region.

4. A plasmid cloning vehicle of claim 2.

5. A phage cloning vehicle of claim 2.

6. The phage cloning vehicle of claim 5, wherein the cloning vehicle is derived from phage M13.

7. The plasmid cloning vehicle of claim 4, wherein the cloning vehicle is derived from the pUC plasmid.

8. A genetically engineered bacterial host cell which comprises the cloning vehicle of claim 2.

9. An *E. coli* host cell of claim 8.

10. An *E. coli* host cell of claim 9 designated JM83 and having ATCC Accession No. 53307.

11. A mammalian host cell which comprises the cloning vehicle of claim 2.

12. A mammalian host cell of claim 11 wherein the mammalian cell is a NIH 3T3 cell.

13. A fused gene which comprises a first DNA molecule encoding a protein fused to said streptavidin encoding DNA molecule of claim 1, wherein the streptavidin has a multiplicity of binding sites for biotin or a biotin derivative, and wherein the fused gene is capable of expressing a fused protein in vivo when said fused gene is inserted into a suitable expression vector and introduced into a suitable host cell.

14. The fused gene of claim 13 wherein the first DNA molecule is at the 5' end of the fused gene.

15. The fused gene of claim 13 wherein the DNA molecule encoding streptavidin is at the 5' end of the fused gene.

16. The fused gene of claim 13, wherein the first DNA molecule is the gene encoding the human LDL receptor protein.

17. The fused gene of claim 16, which is capable of expressing protein that consists of streptavidin at the N-terminal region of the fused protein and the LDL receptor protein at the C-terminal region of the fused protein when the fused gene is inserted into an expression vector and introduced into a host cell.

18. An expression vector capable of expressing the fused gene of claim 13, when introduced into a host cell, which comprises carrier DNA and said fused gene of claim 13 wherein said carrier DNA comprises a promoter and operator region.

19. A mammalian expression vector of claim 18.

20. A mammalian host cell which comprises the expression vector of claim 19.

21. An NIH 3T3 host cell of claim 20.

22. An expression vector capable of expressing the fused gene of claim 16, when introduced into a host cell, which comprises carrier DNA and the fused DNA fragments of claim 16.

23. A mammalian expression vector of claim 22.

24. A mammalian host cell which comprises the expression vector of claim 23.

25. An NIH 3T3 host cell of claim 24.

* * * * *

Notice of Adverse Decisions in Interference

In Interference No. 102,477, involving Patent No. 4,839,293, Charles R. Cantor, Richard Axel, Carlos Argarana, DNA ENCODING STREPTAVIDIN, STREPTAVIDIN PRODUCED THEREFROM, FUSED POLYPEPTIDES WHICH INCLUDE AMINO ACID, SEQUENCES PRESENT IN STREPTAVIDIN AND USES THEREOF, final judgement adeverse to the patentees was rendered Aug. 23, 1991, as to claims 1-25.

*(Official Gazette Oct. 22, 1991)*